United States Patent [19]

Raad et al.

[11] Patent Number: 5,362,754
[45] Date of Patent: Nov. 8, 1994

[54] M-EDTA PHARMACEUTICAL PREPARATIONS AND USES THEREOF

[75] Inventors: Issam Raad, Houston, Tex.; Robert J. Sherertz, Winston-Salem, N.C.

[73] Assignee: Univ. of TX MD Anderson Cancer Center, Houston, Tex.

[21] Appl. No.: 975,486

[22] Filed: Nov. 12, 1992

[51] Int. Cl.$^5$ .................... A01N 25/02; A61M 31/00; A61K 31/195
[52] U.S. Cl. ................... 514/566; 514/836; 424/405; 604/53
[58] Field of Search ............ 424/405, 409, 423; 604/53; 514/836, 566

[56] References Cited

U.S. PATENT DOCUMENTS

| | | | |
|---|---|---|---|
| 4,107,121 | 8/1978 | Stoy | 260/29.6 |
| 4,442,133 | 4/1984 | Greco et al. | 427/2 |
| 4,678,660 | 7/1987 | McGary et al. | 424/25 |
| 4,749,585 | 6/1988 | Greco et al. | 427/2 |
| 4,895,566 | 1/1990 | Lee | 604/266 |
| 4,917,686 | 4/1990 | Bayston et al. | 604/265 |
| 4,952,419 | 8/1990 | De Leon et al. | 427/2 |
| 5,013,306 | 5/1991 | Solomon et al. | 604/265 |
| 5,202,449 | 4/1993 | Hasegawa et al. | 552/206 |
| 5,217,493 | 6/1993 | Raad | 623/11 |

FOREIGN PATENT DOCUMENTS

PCT/US93/-10893 2/1994 WIPO .

OTHER PUBLICATIONS

Root et al "Inhibitory Effect of Disodium EDTA Upon the Growth of *Staphylococcus Epidermis* in Vitro: Relation to Infection Prophylaxis of Hickman Catheters" *Antimicrobial Agents and Chemotherapy*, 32(11):1627–1631, 1988, published in USA.

AHFS Drug Information, 1992 edition, Gerlad K. McEvoy et al., editors, "Minocycline–HC1," pp. 318–319 and Edetate Disodium, pp. 1805–1807, published in USA.

Anwar et al., "Interaction of Biofilm Bacteria with Antibiotics in a Novel In Vitro Chemostat System," *Antimicrobial Agents and Chemotherapy*, 33(10):1824–1826, 1989, published in USA.

Anwar et al., "Tobramycin Resistance of Mucoid *Pseudomonas Aeruginosa* Biofilm Grown Under Iron Limitation," *Jounral of Antimicrobial Chemotherapy*, 24:647–655, 1989, published in Europe.

Clumeck et al., "Treatment of Severe Staphylococcal Infections with a Rifampicin–Minocycline Association," *Journal of Antimicrobial Chemotherapy*, 13(Suppl. C.):17–22, 1984, published in Europe.

Evans and Holmes, "Effect of Vancomycin Hydrochloride on *Staphylococcus Epidermidis* Biofilm Associated with Silicon Elastomer,"*Antimicrobial Agents and Chemotherapy*, 31(6):889–894, 1987, published in USA.

Farber et al., "*Staphylococcus Epidermidis* Extracted Slime Inhibits the Antimicrobial Action of Glycopeptide Antibiotics," *Journal of Infectious Diseases*, 161:37–40, 1990, published in USA.

Goodman and Gilman's The Pharmacological Basis of Therapeutics, Eighth Edition, Pergamon Press, Chapter (List continued on next page.)

Primary Examiner—Thurman K. Page
Assistant Examiner—Carlos Azpuru
Attorney, Agent, or Firm—Arnold, White & Durkee

[57] ABSTRACT

Disclosed are pharmaceutical compositions of a mixture of minocycline and EDTA (M-EDTA) and methods of using the compositions in maintaining the patency of a catheter port. Methods for inhibiting the formation of polysaccharide-rich glycocalyx (such as the glycocalyx of staphylococcal organisms) are also provided using an M-EDTA solution. The M-EDTA solution may also be used to pretreat a medical device to prevent adherence of infectious organisms, such as *S. epidermidis* and *S. aureus*. The compositions destroy and prevent the formation of polysaccharide-rich glycocalyx. Methods for treating infections of *S. epidermidis* and *S. aureus* where glycocalyx formation are provided with an M-EDTA solution. The minocycline and EDTA solutions are included together within a pharmacologically acceptable carrier solution, such as saline.

14 Claims, 11 Drawing Sheets

OTHER PUBLICATIONS

48, "Antimicrobial Agents," pp. 1117–1125, 1607–1608, 1990, published in USA.

Harper and Epis, "Effect of Chlorhexidine/EDTA/Tris Against Bacterial Isolates from Clinical Specimens," *Microbios*, 51:107–112, 1987, published in Europe.

Hoyle et al., "The Biofilm Glycocalyx as a Resistance Factor," *Journal of Antimicrobial Chemotherapy*, 26:1–6, 1990, published in Europe.

Khoury and Costerton, "Bacterial Biofilms in Nature and Disease," *Dialogues in Pediatric Urology*, 14(10):2–5, 1991, published in USA.

Reid, Gregor, "Important Components in the Adhesion of Bacteria to Prosthetic Devices," *Dialogues in Pediatric Urology*, 14(10):6–7, 1991, published in USA.

Nickel, J. Curtis, "Bacterial Biofilms in Urological Infectious Diseases," *Dialogues in Pediatric Urology*, 14(10):7–8, 1991, published in USA.

Machnicka et al., "Influence of 0.02 M EDTA and 3 M Kcl on Surface of *Hymenolepis Diminuta* and Composition of Isolated Proteins," *Folia Histochemica Et Cytobiologica*, 24(1):65–70, 1986, published in Europe.

Marshall, Kevin C., "Biofilms: An Overview of Bacterial Adhesion, Activity, and Control at Surfaces," *ASM News*, 58(4):202–207, 1992, published in USA.

*The Merck Index: An Encyclopedia of Chemicals, Drugs and Biologicals*, Eleventh Edition, Susan Budavari, Editor, Merck & Co., Inc., Publishers, Rahway, N.J., 1989, "Minocycline," p. 976, published in USA.

Nickel et al., "Tobramycin Resistance of *Pseudomonas Aeruginosa* Cells Growing as a Biofilm on Urinary Catheter Material," *Antimicrobial Agents and Chemotherapy*, 27(4):619–624, 1985, published in USA.

*Remington's Pharmaceutical Sciences*, 18th Edition, Alfonso R. Gennaro, Editor, Mack Publishing Company, Easton, Penn., "Minocycline HC1," p. 1213, 1990, published in USA.

Said et al., "Expression of H 1 Outer-Membrane Protein of *Pseudomonas Aeruginosa* in Relation to Sensitivity to EDTA and Polymyxin B," *Journal of Medical Microbiology*, 24:267–274, 1987, published in Europe.

Solomon, Donald D., "Antibiotic Releasing Polymers," *Journal of Controlled Release*, 6:343–352, 1987, published in Europe.

Tojo et al., "Isolation and Characterization of a Capsular Polysaccharide Adhesin from *Staphylococcus Epidermidis*," *The Journal of Infectious Diseases*, 157(4):713–722, 1988, published in USA.

Vergéres and Blaser, "Amikacin, Ceftazidime, and Flucloxacillin Against Suspended and Adherent *Pseudomonas Aeruginosa* and *Staphylococcus Epidermidis* in an In Vitro Model of Infection,"*The Journal of Infectious Diseases*, 165:281–289, 1992, published in USA.

Zinner et al., "Antistaphylococcal Activity of Rifampin with Other Antibiotics," *The Journal of Infectious Diseases*, 144(4):365–371, 1981, published in USA.

Dialog Search Report printed in USA in 1992.

Yourassowsky et al., "Combination of Minocycline and Rifampicin against Methicillin-and Gentamicin-Resistant *Staphylococcus Aureus*," *J. Clin. Pathol.*, 34:559–563, published in Europe.

Segreti et al., "In Vitro Activity of Minocycline and Rifampin Against Staphylococci," *Diagn. Microbiol. Infect. Dis.*, 12:253–255, 1989, published in USA.

Yuk et al. "Minocycline as an Alternative Antistaphylococcal Agent," *Review of Infectious Diseases*, 13:1023–1024, 1991, published in USA.

M-EDTA PHARMACEUTICAL PREPARATIONS AND USES THEREOF

BACKGROUND OF THE INVENTION

1. Field of the Invention

The present invention relates to indwelling medical articles, such as catheters, which may also be flushed or coated with a microbial-inhibiting pharmaceutical preparation. The invention also relates to pharmaceutical preparations useful in maintaining catheter patency and preventing infection. Methods of using the pharmaceutical preparation of the invention in the management and maintenance of a vascular catheter are also related to the present disclosure.

2. Background of the Related Art

Indwelling medical devices including vascular catheters have become essential in the management of hospitalized or chronically ill patients. Unfortunately, vascular catheters have become the major source for hospital-acquired sepsis. Hence, the benefit derived from indwelling medical devices such as vascular catheters is often upset by infectious complications. Thrombotic occlusions of the lumen of central venous catheters (CVC) is another complication that will often lead to the removal of catheters.

The current standard care of catheters includes flushing the lumen of the catheter with heparin. However, heparin has no antimicrobial activity. Thus, infections, as well as thrombotic occlusion, continue to occur frequently despite the prophylactic use of heparin flushes. Knowledge of the pathogenesis and microbiology of central venous catheter-related infections is essential in order to provide effective prevention for this problem. Three essential factors must be considered in controlling for catheter colonization by infectious microbes. The first is controlling the availability of microorganisms that adhere to the inert catheter surface. Such microorganisms typically include such staphylococci and candida. The second is control of the production slimy polysaccharide known as fibrous glycocalyx, by adherent microbial organisms. Production of the glycocalyx is essential for the adherence and integrity of these organisms. The third is control of the formation of the thrombin sheath by the host, which acts to engulf the catheter. The thrombin sheath provides the microorganisms a sticky substrate for enhanced adherence to the catheter, and thus, continued colonization and infection at the catheter site. The present inventors herein disclose an M-EDTA solution unique in its ability to inhibit all three of these essential conditions, and thus provide effective methods for controlling catheter-related infection and onset thereof.

*Staphylococcus epidermidis* and *S. aureus* account for 75% of CVC related infections. Candida species account for another 10% to 15% of such infections. The use of antistaphylococcal antibiotics to prevent these infections has been found to reduce CVC related bacterial infections, but only at the expense of the occurrence of higher rates of fungal (Candida) infections. The fibrous glycocalyx material produced by staphylococci and Candida helps these organisms adhere and stick to catheter surfaces, thus exacerbating the problem of eliminating these types of infections after they have become established. These microbial biofilm layers are made of a fibrous glycocalyx material primarily polysaccharide in nature. The protective sheath provided by the glycocalyx at the infected site effectively prevents the elimination and treatment of these infections. Preparation effective for destroying such a glycocalyx would, therefore, provide a solution to treating established catheter infections where a glycocalyx has already been allowed to form.

Compositionally distinct glycocalyx material is produced by a variety of different organisms. For example, the glycocalyx produced by *Hymenolepis diminuta* is reportedly eliminated upon treatment with 0.02 M-EDTA or 3M KCl[12]. However, the particular glycocalyx of *Hymenolepis diminuta* (tapeworm) is compositionally mostly proteins[12], which is distinct from the material of the glycocalyx typical of those organisms that colonize and cause catheter infection. For example, the glycocalyx of several staphylococcus species comprise primarily polysaccharides with only low to nondeductible levels of protein[13] (Tojo et al. at pg. 716, Table 1). Glycocalyx of microorganisms common to catheter infection are thus compositionally distinct from the organic composition of glycocalyx of such organisms as the tapeworm, *Hymenolepis diminuta*. A pharmaceutical preparation effective for reducing or eliminating glycocalyx of infectious microorganisms typically associated with catheter colonization and infection has yet to be identified.

Infectious microorganisms will typically embed themselves in the protective layer of the glycocalyx, thus providing a shield or hiding place that protects staphylococci and fungi from the activity of phagocytic cells. An agent or composition that would dissolve or prevent biofilm formation of these clinically important pathogens would thus provide a major breakthrough in the prevention of the typical catheter-related Staphylococcal and Candida infections that plague humans.

There has also been observed to be a correlation between thrombogenesis and infection. Essentially, indwelling vascular catheters get engulfed by a fibrin sheath that subsequently acts to cover the internal and external surfaces of a catheter. This fibrin sheath provides such organisms as Staphylococci and Candida, with an enhanced adherence capacity to the catheter surface. Unlike these particular microbes gram-negative bacilli do not adhere well to fibrin and fibronectin. A composition that halted fibrin formation would thus be particularly useful in halting the colonization of these microbes at indwelling catheter sites.

Intraluminal colonization through a catheter hub also constitutes a prelude to catheter-related infections and septicemias in long-term CVC. The inventors study presented herein of 359 long-term CVC patients (all of which were studied by quantitative catheter culture) demonstrates that CVC's with positive cultures as well as matched negative controls evidenced colonization (as quantitated by EM) and biofilm formation of the internal surface at least twice greater than that of external surface with catheters that stayed longer than 10 days in place. This data is from nontunneled, noncuffed percutaneous CVC. For tunneled CVCs (Hickman/Broviac) and ports, internal colonization was even more prominent. The development of an anticoagulant pharmaceutical preparation effective against staphylococci, fungi, and polysaccharide-rich glycocalyx formation would thus provide a solution to the treatment and elimination of thrombogenesis and the septicemia associated with long-term CVC.

EDTA is a well known anticoagulant used in blood collection tubes. It is also well known to have an antibacterial and antistaphylococcal effect (alone or in combination)[1-3]. Root[9] even compared to the efficacy of EDTA for use with vascular catheters as an antibacterial agent to heparin alone and a vancomycin-heparin preparation in vitro. While those investigators found EDTA to be bacteriocidal, no remedy or suggestion of how the microbial glycocalyx of a device-related infection could be eliminated was observed or described.

Although glycopeptide antibiotics (vancomycin and teicoplanin) are active against staphylococci in vitro and in tissue, they are not active against adherent staphylococci embedded in a biofilm layer, such as glycocalyx. While flushing with such agents may acutely destroy these microorganisms, the risk of rapid development of tolerant and resistant strains in the patient being treated makes this a contraindicated procedure in most cases. In addition, patients developing such vancomycin-tolerant or resistant strains bacteremias would be left without an antibiotic that could be used therapeutically.

Based on all of the above, the ideal prophylactic agent for catheter maintenance would both inhibit or eliminate the formation of polysaccharide-rich glycocalyx of such microorganisms as well as the staphylococci and fungi leading to the prevention of infection at a catheter surface.

It is an object of the invention to provide both an anti-staphylococcal and antifungal (anti-Candida) active agent effective against free-floating as well as adherent organisms embedded in biofilm, as well as to provide an anticoagulant agent and/or method that would prevent and alter/dissolve a polysaccharide-rich fibrous glycocalyx biofilm layer. Such a pharmaceutical agent would optimally provide an anticoagulant that would prevent thrombotic occlusion of the catheter lumen as well as thrombin formation that is the substrate for catheter infection. Additional objects of the invention include providing an agent that could be given intraluminally without a toxicity concern to humans and would provide a method that would kill adherent staphylococci and Candida. Such methods would preferably not be the same agent a clinician would use therapeutically (such as Vancomycin, Ampho B, or Azoles).

The present invention demonstrates that a mixture of minocycline/disodium EDTA (referred to as M-EDTA) does fulfill all of the listed objects.

SUMMARY OF THE INVENTION

The present invention provides a unique and effective pharmaceutical preparation that includes minocycline and EDTA for maintaining the patency of a catheter.

The EDTA of the preparation provides potent glycocalyx inhibiting potential, while the minocycline at high concentrations has a fungicidal effect together with the unique ability to penetrate a polysaccharide-rich glycocalyx biofilm layer. The combination of minocycline-EDTA thus provides a unique anticoagulant, anti-microbial, glycocalyx inhibiting, antibacterial and antifungal agent for the prevention of thrombogenesis, microbial adherence and device-related infections.

The inventors have shown that minocycline's penetration of the microbial biofilm layer is at least 6-fold higher than vancomycin. The inventors also demonstrate that EDTA is unique in effectively preventing and dissolving polysaccharide-rich microbial glycocalyx.

The inventors disclose a unique method of using minocycline as an ideal antimicrobial agent. Compositions that further include EDTA with minocycline are also useful in the described methods. Minocycline is demonstrated to kill adherent staphylococci (embedded in glycocalyx—Example 4). Minocycline is demonstrated by the present inventors to be superior to vancomycin. Vancomycin is currently the standard antibiotic used in the treatment of *Staphylococcus epidermidis* and resistant *Staphylococcus aureus*. The preparation of the present invention in one aspect may further comprise a mixture of a pharmacologically effective amount of minocycline and EDTA in a pharmacologically acceptable carrier solution.

For use in maintaining catheter patency, the pharmaceutical preparation of the invention may be efficaciously used with such medical devices as a central venous catheter, a peripheral intervenous catheter, an arterial catheter, a Swan-Ganz catheter, a hemodialysis catheter, an umbilical catheter, a percutaneous nontunneled silicone catheter, a cuffed tunneled central venous catheter as well as with a subcutaneous central venous port.

For the herein described uses, a solution of the M-EDTA may be prepared containing a concentration of between about 10-100 mg/ml EDTA (preferably between 20-60 mg/ml) and between about 0.001-100 mg/ml minocycline (preferably 2-9 mg/ml). Most preferably, the preparation includes about 30 mg/ml EDTA and about 3 mg/ml minocycline reconstituted from 100 mg vial of minocycline (Minocin Intravenous, Lederle (Carolina, Puerto Rico). The carrier solution, by way of example, may comprise saline.

In one particular aspect of the invention, a catheter flushing pharmaceutical preparation is provided. Most preferably, the catheter flushing pharmaceutical preparation comprises a glycocalyx inhibiting concentration of EDTA and minocycline in a pharmaceutically acceptable carrier solution. More specifically, the concentration of EDTA in the preparation is between about 10-100 mg/ml with the concentration of minocycline being between 0.001-100 mg/ml in the preparation.

A "glycocalyx inhibiting concentration" is defined for purposes of describing the present invention as a concentration effective to degrade, dissolve, or otherwise inhibit a polysaccharide-rich glycocalyx. By way of example, such a polysaccharide-rich glycocalyx is characteristic of established staphylococcal infections of *S. aureus* and *S. epidermidis*.

The catheter flushing pharmaceutical preparation of the invention may be described more particularly as including about 30 mg/ml EDTA and about 3 mg/ml minocycline. By way of example, the carrier solution is saline. The catheter flushing preparation of the present invention may advantageously be used to inhibit the formation of polysaccharide-rich glycocalyx. In this manner, infections characterized by such a formation may be effectively eliminated.

Another aspect of the present invention provides, a method of preparing a biofilm-resistant device. The method in one embodiment comprises coating a device with the pharmaceutical solution described herein or with the catheter flushing pharmaceutical preparation aforedescribed. While the method may be used to coat virtually any surface where glycocalyx formation is to be desirably inhibited, use of the method in preparing a microbial biofilm-resistant catheter device is particularly envisioned. It is anticipated that the method will provide a device resistant to polysaccharide-rich glycocalyx formation, such as that typical of Staphylococci. Any of a variety of catheters may be treated or coated according to the described method employing coating techniques well known to those of skill in the art. By way of example, catheters that may be prepared and treated according to the invention include a central venous catheter and a triple lumen catheter.

In still another aspect of the present invention, a method for preparing a biofilm-resistent medical device using a pharmaceutical preparation of minocycline and EDTA is provided. The method comprises preparing a pharmaceutical preparation of minocycline and sodium EDTA in a biocompatible adherent coating carrier solution and treating the surface of the medical device of interest with the pharmaceutical preparation for a period of time sufficient to allow the formation of a film of the preparation to the surface of the device. Most preferably, the method is to be used in preparing a biofilm-resistent catheter.

As used in the description of the present invention, a "biofilm-resistent" device or surface is defined as a surface or device that will prevent the adherence or growth of organisms that produce polysaccharide-rich glycocalyx material. Such organisms include the *Staphylococcal aureus* and *epidermidis* species. However, any organism that produces a polysaccharide-rich glycocalyx material would be equally inhibited by the herein described devices, surfaces and pharmaceutical preparations.

The pharmaceutical preparation of the method in a particularly preferred embodiment is further described as comprising about 3 mg/ml minocycline and about 30 mg/ml EDTA.

The present invention also provides a method for inhibiting glycoprotein-rich glycocalyx formation at a catheter port. The method in one embodiment comprises flushing the catheter periodically with a pharmaceutical preparation comprising a glycocalyx-inhibiting concentration of EDTA and minocycline in a pharmacologically acceptable carrier solution. In one aspect of the method, the glycocalyx-inhibiting concentration of EDTA is between 10 mg/ml and 100 mg/ml. The most preferred concentration of EDTA is about 30 mg/ml. According to one aspect of the described method, the catheter may be described as a tunneled catheter or an untunneled catheter. As part of a catheter maintenance regimen, the catheter most preferably is to be flushed with the aforedescribed preparation at least once every 24 hours. In still another aspect of the method, the pharmaceutical preparation includes minocycline. Where minocycline is inducted in the preparation, the glycocalyx inhibiting concentration of minocycline may also be further defined as constituting a concentration of between about 0.001 mg/ml and 100 mg/ml. The most preferred concentration of minocycline is about 3 mg/ml.

In still another aspect of the invention, a method for eliminating microbial glycocalyx formation, particularly polysaccharide-rich (Staphylococcal) glycocalyx formation, at a catheter lumen is provided. The method, in one embodiment, comprises preparing a solution consisting essentially of minocycline and EDTA in a carrier solution to provide an M-EDTA preparation, and flushing the catheter with a therapeutically effective amount of the M-EDTA preparation. In one embodiment, the M-EDTA preparation includes a concentration of minocycline of between about 0.001–100 mg/ml (preferably 2–9 mg/ml) and between about 10–100 mg/ml (preferably 20–60 mg/ml) EDTA. The therapeutically effective amount of the aforedescribed M-EDTA preparation would, therefore, constitute between about 1–10 ml (preferably about 2–3 ml) of the solution.

Most preferably, the catheter will be flushed with a volume of about 3 ml of the aforedescribed M-EDTA preparation containing about 30 mg/ml EDTA and about 3 mg/ml minocycline. The catheter is to be flushed periodically at about 24 hour intervals with between about 2–3 ml of the M-EDTA preparation. In a preferred aspect of the method, the catheter is to be flushed more frequently at 4 hour intervals with the herein described preparations of M-EDTA. The preparation will remain therapeutically effective for use as a catheter-flushing agent stored at a refrigerated temperature for at least 1 month after formulation. In addition, the M-EDTA solution should be brought to room temperature before use on an animal or patient.

The aforedescribed preparations have been found effective in preventing the adherence and colonization of catheter surfaces by *S. aureus, S. epidermidis*, and fungi, as well as effective in both treating and eliminating already formed glycocalyx formations of these infectious organisms.

The following abbreviations are used in the description of the present invention:
CVC=Central Venous Catheters
MRD=Modified Robbins Device
M-EDTA=minocycline-EDTA mixture
$D_{10}/W$=10% Dextrose and Water

DETAILED DESCRIPTION OF THE PREFERRED EMBODIMENTS

Figure 1:
FIG. 1—Scanning electron microscopy picture showing staphylococci and biofilm from a control catheter segment that was exposed to slime producing *S. epidermidis* and later immersed in Dextrinase for 24 hours. (Example 6 results.)

The present invention provides a pharmaceutically effective formulation of minocycline and EDTA. These formulations have been found by the present inventors to be particularly useful in preventing the formation of the "biofilm" or polysaccharide-rich glycocalyx that typically accompanies microbial surface colonization. In particular, the formulations are most effective in breaking down staphylococcal glycocalyx and in inhibiting its formation. This feature makes the preparations of the present invention potentially useful in the treatment of staphylococcal infections where a polysaccharide-rich glycocalyx has formed or may potentially be formed, as well as in the prevention and treatment of Staphylococcal and Candida infection.

The present invention also provides M-EDTA-treated or coated medical devices, such as catheters, that prevent staphylococcal or fungal colonization.

The minocycline used in the studies described in the present disclosure was obtained from Lederle (Minocin ®) (intravenous, 100 mg, Carolina, Puerto Rico). The disodium-EDTA used in the studies described in the present disclosure was obtained from Abbott Co. (Endrate ® (Intravenous 150 mg/ml) Chicago, Ill.). A Modified Robbin's Device, a screening tool customarily used and accepted as predictive of catheter use in humans[15,16], was used in the present study of the M-EDTA pharmaceutical preparations described. The model was constructed at M. D. Anderson Cancer Center in Houston, Tex.

The following agents were used in the studies disclosed herein:

| SUBSTANCE | BRAND NAME | SOURCE | LOCATION |
|---|---|---|---|
| Urokinase | Abbokinase | Abbott Laboratories | Chicago, IL |
| Heparin | — | Sigma Chemical Co. | St. Louis, MO |
| Saline | 0.09 Sodium Chloride (injection U.S.P.) | Baxter Healthcare Corp. | Deerfield, IL |
| Dextrinase | — | Sigma Chemical Co. | St. Louis, MO |
| Vancomycin | Lyphocin Intravenous, 1 gram | Lyphomed | Rosemont, IL |
| Trypticase Soy broth | — | DIFCO Laboratories | Detroit, MI |

Even though the invention has been described with a certain degree of particularity, it is evident that many alternatives, modifications, and variations will be apparent to those skilled in the art in light of the present disclosure. Accordingly, it is intended that all such alternatives, modifications, and variations which fall within the spirit and the scope of the invention be embraced by the defined claims.

The following examples are presented to describe preferred embodiments and utilities of the present invention, but should not be construed as limiting the claims thereof.

EXAMPLE 1—PREPARATION OF M-EDTA PHARMACEUTICAL PREPARATION

The present example provides a detailed description of how the M-EDTA pharmaceutical preparation is to be prepared. EDTA was obtained from Sigma. The minocycline was obtained from Lederle. A solution of M-EDTA was prepared as described herein to a concentration of 3 mg/ml minocycline and 30 mg/ml EDTA. The M-EDTA preparation was formulated in a sterile saline solution.

The M-EDTA solution was prepared as follows:
about 60 mg/ml of EDTA (reconstituted from 200 mg/ml Edetate Calcium Disodium (Versenste ®, 3M Riker, Northridge, Calif.) or reconstituted from Edetate Disodium (150 mg/ml parenteral concentrate (Endtrate ®, Abbott, Chicago, Ill., or Disotate ®, Forest, Maryland Heights, Mo.). In addition, the 60 mg/ml of EDTA could be reconstituted from EDTA powder (Sigma Chemical Co., St. Louis, Mo.).

The 6 mg/ml minocycline and 60 mg/ml EDTA are then to be mixed in equal volumes to constitute a 3 mg minocycline and 30 mg EDTA/ml solution. The solution is then to be brought to a physiologically acceptable pH of about 7.4. The solution is to be stored in a sterile container at a temperature of about 4° C. until use.

Figure 11A:
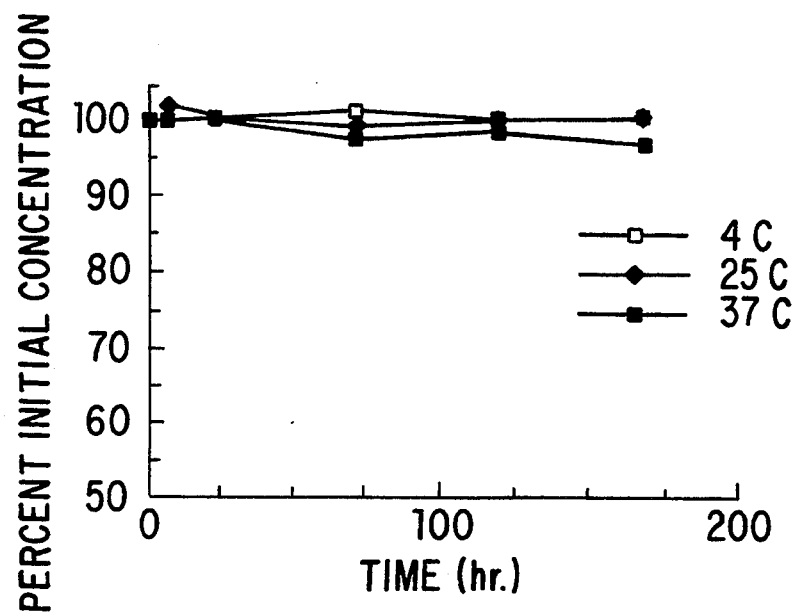
FIG. 11—EDTA Stability (A) and Minocycline Stability (B).
Figure 11B:
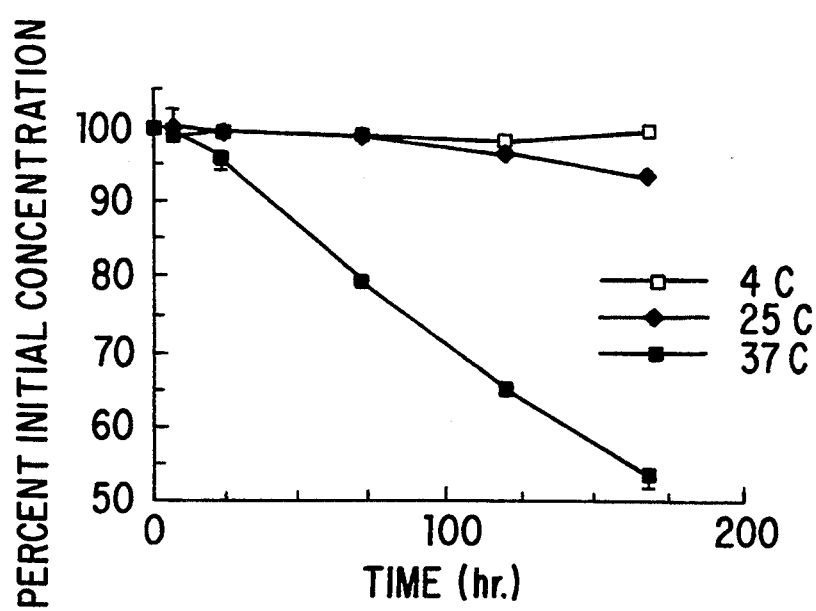

Once formulated, the M-EDTA may be stored refrigerated at 4° C. until use. It is contemplated that so formulated, the solution will remain chemically stable and pharmacologically active for at least 1 month at 4° C. The preparation is also very stable at room temperature (37° C.) for at least 72 hours (Table 1 and FIG. 11). The preparation should be at room temperature before administration to a patient.

TABLE 1

Percentage of Initial Concentration Remaining* of Calcium Disodium Versenate (EDTA) 30.0 mg/mL and Minocycline Hydrochloride 3 mg/mL in a Catheter Flush Solution. Detected by High Power Liquid Chromotography.

| Temperature (C.) | Storage time (hr) | | | | | |
|---|---|---|---|---|---|---|
| | 0 | 6 | 24 | 72 | 120 | 168 |
| EDTA | | | | | | |
| 37 | 100.0 ± 0.5 | 99.9 ± 0.6 | 100.3 ± 0.2 | 97.9 ± 0.4 | 99.0 ± 0.5 | 96.9 ± 0.2 |
| 25 | 100.0 ± 0.5 | 102.1 ± 0.3 | 100.9 ± 0.0 | 100.1 ± 0.1 | 100.4 ± 0.2 | 100.5 ± 0.2 |

TABLE 1-continued

Percentage of Initial Concentration Remaining* of Calcium Disodium
Versenate (EDTA) 30.0 mg/mL and Minocycline Hydrochloride 3 mg/mL in a
Catheter Flush Solution. Detected by High Power Liquid Chromotography.

| Temperature (C.) | Storage time (hr) | | | | | |
|---|---|---|---|---|---|---|
| | 0 | 6 | 24 | 72 | 120 | 168 |
| 4 | 100.0 ± 0.5 | 100.2 ± 0.1 | 100.8 ± 0.2 | 101.7 ± 0.8 | 100.3 ± 0.1 | 100.9 ± 0.4 |
| Minocycline Hydrochloride | | | | | | |
| 37 | 100.0 ± 0.2 | 99.76 ± 0.0 | 96.0 ± 1.3 | 79.9 ± 0.7 | 65.4 ± 1.0 | 53.5 ± 1.3 |
| 25 | 100.0 ± 0.2 | 100.5 ± 1.9 | 99.4 ± 0.8 | 98.7 ± 0.5 | 96.8 ± 0.5 | 93.8 ± 0.6 |
| 4 | 100.0 ± 0.2 | 98.9 ± 0.4 | 99.7 ± 0.5 | 98.8 ± 0.7 | 98.3 ± 0.6 | 99.8 ± 0.1 |

Mean of duplicate determinations ± S.E.M.

EXAMPLE 2

An in vitro model consisting of the Modified Robbin's Device (MRD) was used to study the formation of biofilm and colonization of catheter segments of S. Epidermidis. This is a well established model that is described in Nickel et al.[15] and Evans and Holmes[16], and provides a study model recognized by those of skill in the art as predictive of in vivo effects at a catheter surface.

The MRD is constructed of an acrylic block, 42 cm long, with a lumen of $2 \times 10$ mm. The MRD is made of twenty-five evenly spaced specimen plugs each connected to a catheter latex segment whose anterior surface (0.3 cm$^2$) comes in contact with the flushed infusate coming from a connected tubing and infusion bag. Several studies were conducted using this model, which are outlined in the following examples.

EXAMPLE 3

The present example is provided to demonstrate the utility of the present invention for inhibiting S. epidermidis in and on a catheter. The in vitro model described in Example 2 was used in the study. The present example will demonstrate the utility of the present invention for the treatment and maintenance of catheter patency in vivo, and more specifically for inhibiting S. epidermidis adhesion and glycocalyx formation at a catheter surface.

Catheter segments were placed in the specimen plugs of the Modified Robbins Device described in Example 2. After placing the catheter segments in the specimen plugs, the entire apparatus was sterilized with ethylene oxide. A 500 ml 10% dextrose/water bag was infected with $4 \times 10^8$ CFU/ml of S. epidermidis (to produce $8 \times 10^5$ CFU per ml of $D_{10}$/W). The infected infusate was flushed through the MRD for 3 hours at a 50 ml/hr (using a peristaltic pump). In order to remove all free floating and loosely adherent staphylococci, the infected bag was removed and a new sterile bag (of $D_{10}$/W) was used to flush the MRD. The MRD was flushed with sterile $D_{10}$/W for 24 hours at 40 mls/hr. Following this, catheter segments of equal size were treated with different agents by placing them in tubes containing one of the following solutions:

1. Urokinase (5000 units/ml);
2. Heparin (1000 unit/ml);
3. EDTA (50 mg/ml ); and
4. Trypsin (20,000 units/ml) .

Representative catheter segments were then removed (in a sterile manner) at 4 and 24 hours and quantitatively cultured using the scrape-sonication technique described by Khoury et al. (1991)[14] to isolate organisms adherent to catheter surfaces. The Khoury et al. reference is specifically incorporated herein by reference for this purpose. The experiment was done at 37° C.

The results from this study are presented at Table 1. The results demonstrate that treatment of catheter surfaces with EDTA was effective in preventing adherent S. epidermidis colonies on a catheter surface after only 4 hours of treatment. In contrast, urokinase, heparin and trypsin treatment of the catheter segments was significantly less effective at inhibiting adherent S. epidermidis colony formation and adherence after 4 hours of treatment.

TABLE 2

| | No. of adherent S. epidermidis colonies obtained from 0.3 cm$^2$ catheter surfaces | |
|---|---|---|
| Agent Used | After 4 hrs. of treatment | After 24 hrs. of treatment |
| Urokinase | 310 | 40 |
| Heparin | 545 | 20 |
| EDTA | 0 | 0 |
| Trypsin | 150 | 5 |

EXAMPLE 4—M-EDTA AND THE PREVENTION OF BIOFILM FORMATION

The present example is provided to demonstrate the utility of the M-EDTA preparation in preventing staphylococcal biofilm formation at the surface of a catheter, as well as to demonstrate the anti-staphylococcal activity of the preparation at high staphylococcal concentrations.

The method of Example 2 was used with the following modifications:

1. A more intense exposure to staphylococci (S. epidermidis and S. aureus) was achieved by flushing the MRD for 6 hours (instead of 3 hours in Example 3) with $3 \times 10^6$ CFU of staphylococci per ml of $D_5$/W; and
2. The growth of adherent staphylococci to the catheter segments was promoted and achieved by exposing the catheter segments at 37° C. to a 10% broth solution (prepared by adding 1 ml of trypticase soy broth to 9 ml of sterile $H_2O$) of EDTA (30 mg/ml of 10% broth solution), Heparin (100 units/ml of 10% broth), Urokinase (5000 units/ml of 10% broth), minocycline (3 mg/ml of 10% broth), mino/EDTA (30 mg/3 mg per ml of 10% broth), vancomycin (3 mg/ml of 10% broth), vancomycin/heparin (3 mg vanc plus 100 units heparin/ml of 10% broth), or $D_5$/10% broth (50 mg/ml of 10% broth solution).

The results from these studies are demonstrated at Table 2 (S. epidermidis) and Table 3 (S. aureus).

TABLE 3

No. of adherent *S. epidermidis* colonies obtained from 0.3 cm² catheter surfaces

| Agent Used | After 4 hrs. of treatment | After 24 hrs. of treatment |
|---|---|---|
| Urokinase | >5 × 10³ | >5 × 10³ |
| Heparin | >5 × 10³ | >5 × 10³ |
| EDTA | 800 | 20 |
| Minocycline | 10 | 0 |
| Minocycline/EDTA | 0 | 0 |
| Vancomycin | 55 | 85 |
| Vancomycin/Heparin | 445 | 40 |
| D$_5$/10% broth | >5 × 10³ | >5 × 10³ |

As demonstrated in Table 3, the urokinase, heparin and dextrose solutions alone were equally ineffective in preventing and irradicating *S. epidermidis* adherence after 4 or 24 hours of catheter treatment. The minocycline and minocycline/EDTA provided effective prevention and irradication of *S. epidermidis* adhesion after only 4 hours of treatment. Minocycline/EDTA was slightly more effective than minocycline alone at 4 hours. EDTA alone and vanco/heparin provided minimal prevention at 4 hours but were more effective after 24 hours. Vancomycin alone provided equal partial prevention at 4 and 24 hours. M-EDTA was superior to all including vancomycin, vancomycin/heparin, minocycline or EDTA alone.

TABLE 4

No. of adherent *S. aureus* colonies obtained from 0.3 cm² catheter surfaces

| Agent Used | After 4 hrs. of treatment | After 24 hrs. of treatment |
|---|---|---|
| Urokinase | >5 × 10³ | >5 × 10³ |
| Heparin | 256 | >5 × 10³ |
| EDTA | 750 | 30 |
| Minocycline | 0 | 0 |
| Minocycline/EDTA | 0 | 0 |
| Vancomycin | 605 | 230 |
| Vancomycin/Heparin | 140 | 185 |
| D$_5$/10% broth | >5 × 10³ | >5 × 10³ |

*All staphylococcus isolates were bloodstream slime-producing isolates obtained from human patient cases with catheter-related bacteremia.

Table 4 demonstrates that minocycline and minocycline/EDTA solutions were the most effective inhibitors of *S. aureus* adhesion, with 0 adherent colonies being observed after 4 hours of treatment. EDTA alone, vancomycin alone and vancomycin/heparin were significantly less effective for preventing adherent *S. aureus*. These later three preparations had some partial anti-adherent activity, particularly after 24 hours of treatment.

These data (Table 3 and Table 4) demonstrate that minocycline alone or in combination with EDTA was effective for inhibiting *S. epidermidis* and *S. aureus* adherence and colonization of a catheter surface.

EXAMPLE 5—M-EDTA AND THE INHIBITION OF *C. albicans* ADHESION

The present example is provided to demonstrate the utility of the M-EDTA formulation in the inhibition of other glycocalyx and biofilm-forming microorganisms, such as the *C. albicans* of the present study.

The M-EDTA formulation described in Example 1 was employed in the present example. The method employed was identical to that described at Example 4. The organism used was a *C. albicans* obtained from the bloodstream of a patient with catheter-related candidemia. The infected infusate consisted of D$_5$/W with 4×10² CFU of *C. albicans* per ml flushed through the MRD for 6 hours. Results from the study are presented in Table 5.

TABLE 5

No. of adherent *C. albicans* obtained from 0.3 cm² catheter surfaces

| Agent Used | After 4 hrs. of treatment | After 24 hrs. of treatment |
|---|---|---|
| Urokinase | >5 × 10³ | >5 × 10³ |
| Heparin | >5 × 10³ | >5 × 10³ |
| EDTA | 1060 | 155 |
| Minocycline | 190 | 535 |
| Minocycline/EDTA | 0 | 0 |
| D$_5$/10% broth | >5 × 10³ | >5 × 10³ |
| Vancomycin/heparin | >5 × 20³ | >5 × 10³ |
| Vancomycin | 470 | >5 × 10³ |

This example provides the justification for selecting minocycline/EDTA as a unique antistaphylococcal and antifungal agent. Vancomycin (a standard antistaphylococcal agent) when used alone or with heparin failed to have any anti-*C. albicans* activity and was not different from dextrose, urokinase or heparin solutions against *C. albicans*.

EDTA alone had some anti-*C. albicans* activity after 24 hours and minocycline alone had some activity at 4 and probably 24 hours. Both in combination (M-EDTA) were synergistic and had an essentially total inhibitory effect against fungal adherence after 4 and 24 hours. Therefore, M-EDTA is unique in preventing staphylococcal and Candida adherence to catheter surfaces (Staphylococci and Candida contributing to 95% to 100% of the pathogenic microbiology of catheter-related infections).

These results demonstrate that the solutions of a mixture of minocycline and EDTA provide a more effective and rapidly-acting preparation for the prevention of *S. epidermidis*, *S. aureus*, and *C. albicans* adhesion to a catheter surface than any other thrombolytic (urokinase), anticoagulant (heparin, EDTA), or antistaphylococcal preparation (minocycline, vancomycin, vancomycin/heparin).

EXAMPLE 6—*S. epidermidis* BIOFILM FORMATION AND HEPARIN, UROKINASE AND DEXTRINASE TREATMENT The present example is provided to examine the relative *S. epidermidis* biofilm-destroying activity of heparin, urokinase and dextrinase as assessed by scanning electron microscopy of an *S. epidermidis*-colonized catheter surface.

Figure 2:
FIG. 2—Scanning electron microscopy picture showing a layer of biofilm from a catheter segment that exposed to slime producing *S. epidermidis* and later immersed in Urokinase for 24 hours. (Example 6 results.)
Figure 3:
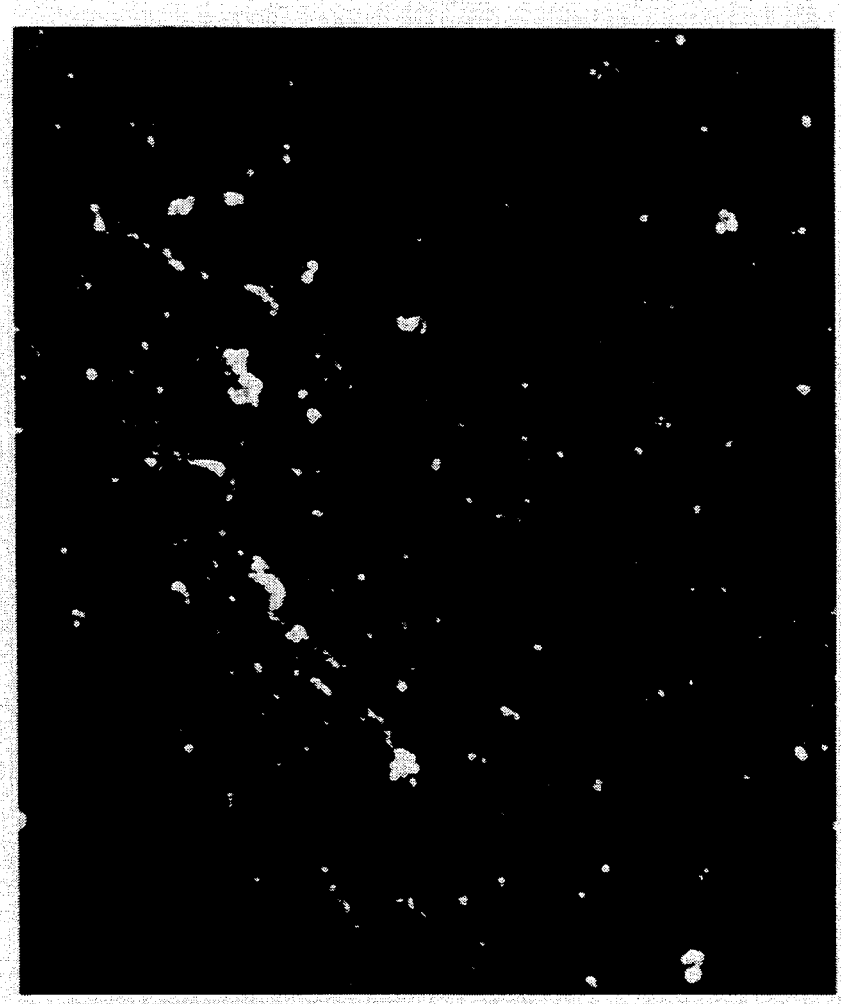
FIG. 3—Scanning electron microscopy picture showing a representative clear surface from a catheter segment exposed to slime producing *S. epidermidis* and later immersed in EDTA for 24 hours. The white particles are dust particles. (Example 6 results.)
Figure 4:
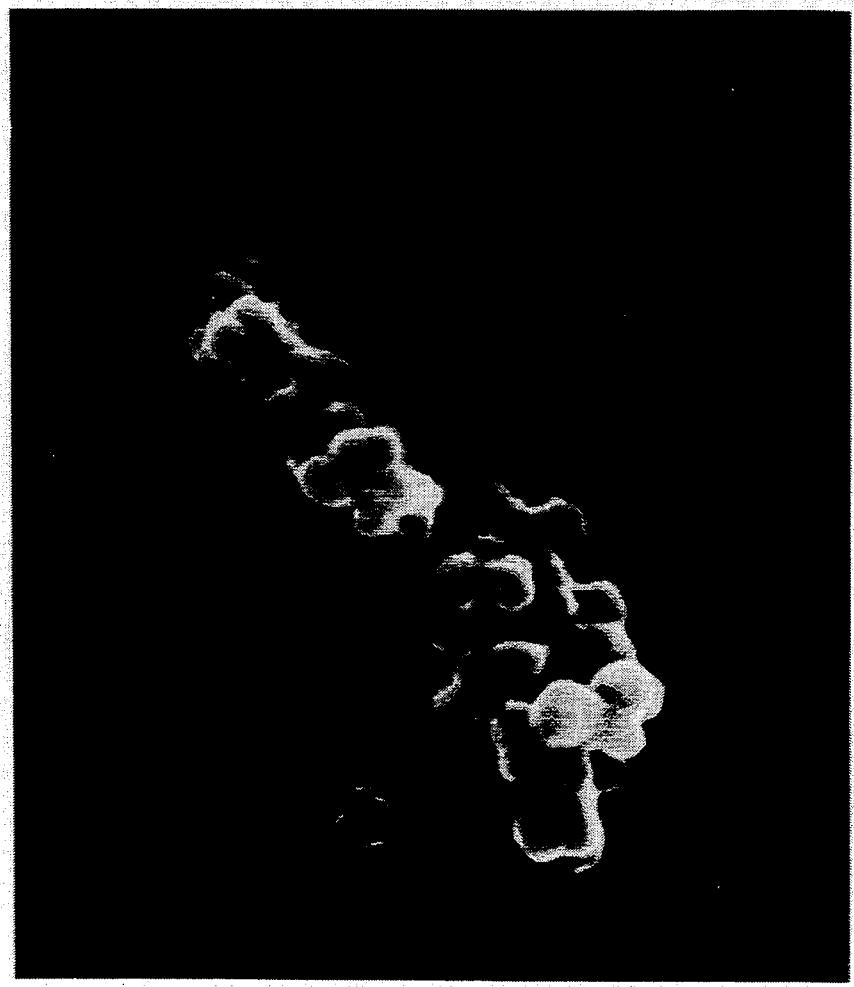
FIG. 4—A scanning electron micrograph at high magnification showing coccal forms in a biofilm layer from a catheter segment coated with control solution (saline) and later exposed to slime producing *S. epidermidis*. (Example 7 results.)

Scanning electron microscopy was done on various segments of a catheter exposed to *S. epidermidis* and then later exposed to heparin, urokinase or dextrinase for 24 hours. A reduction in biofilm (glycocalyx) was noted on colonized catheter surfaces exposed to EDTA for 24 hours, compared to colonized surfaces later exposed to heparin, urokinase, or dextrinase for 24 hours (FIG. 1=Dextrinase; FIG. 2=Urokinase; FIG. 3=EDTA; FIG. 4=Saline).

EXAMPLE 7—PRETREATMENT OF CATHETER SURFACES WITH EDTA, DEXTRINASE OR SALINE AND *S. epidermidis* BIOFILM FORMATION The present example is provided to demonstrate the effect of chemically pretreating a catheter surface with EDTA or dextrinase, compared to a saline control, on biofilm formation and adhesion of *S. epidermidis* to the catheter surface.

Catheter surfaces were coated with EDTA, dextrinase or control (saline), at the concentrations described in Example 5, and then exposed to slime producing *S. epidermidis*.

Figure 5:
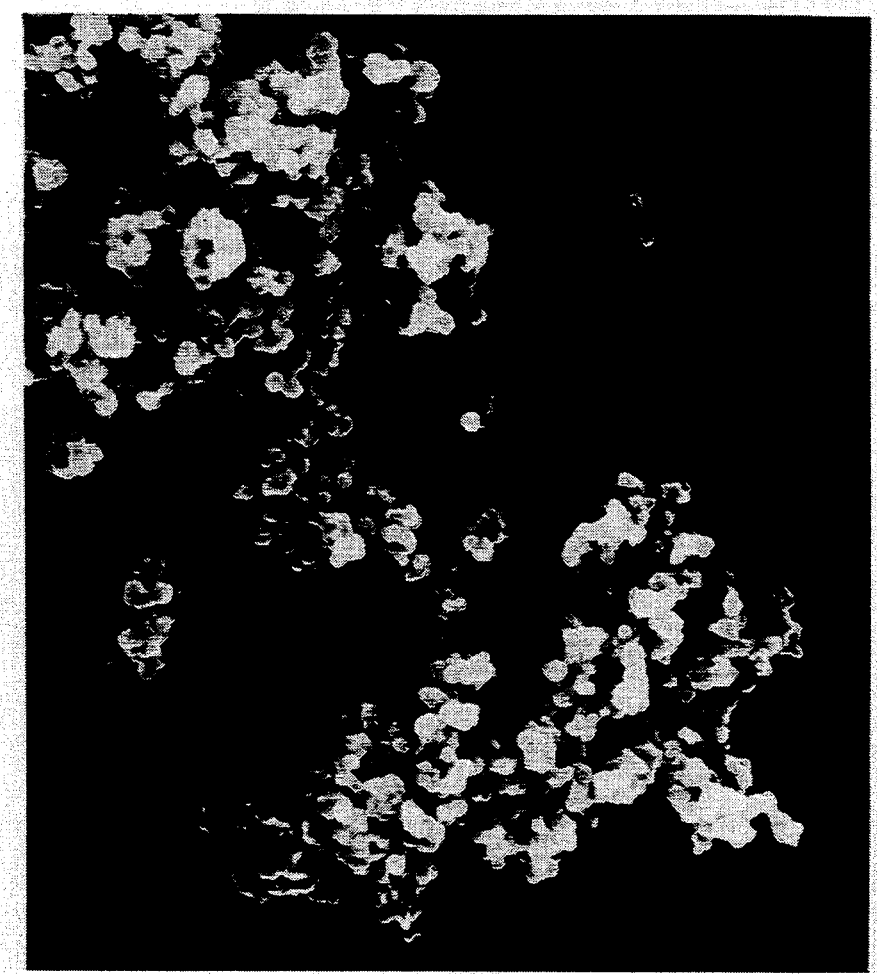
FIG. 5—Lower magnification from a different area of the catheter of FIG. 4 showing coccal forms and biofilm. (Example 7 results.)
Figure 6:
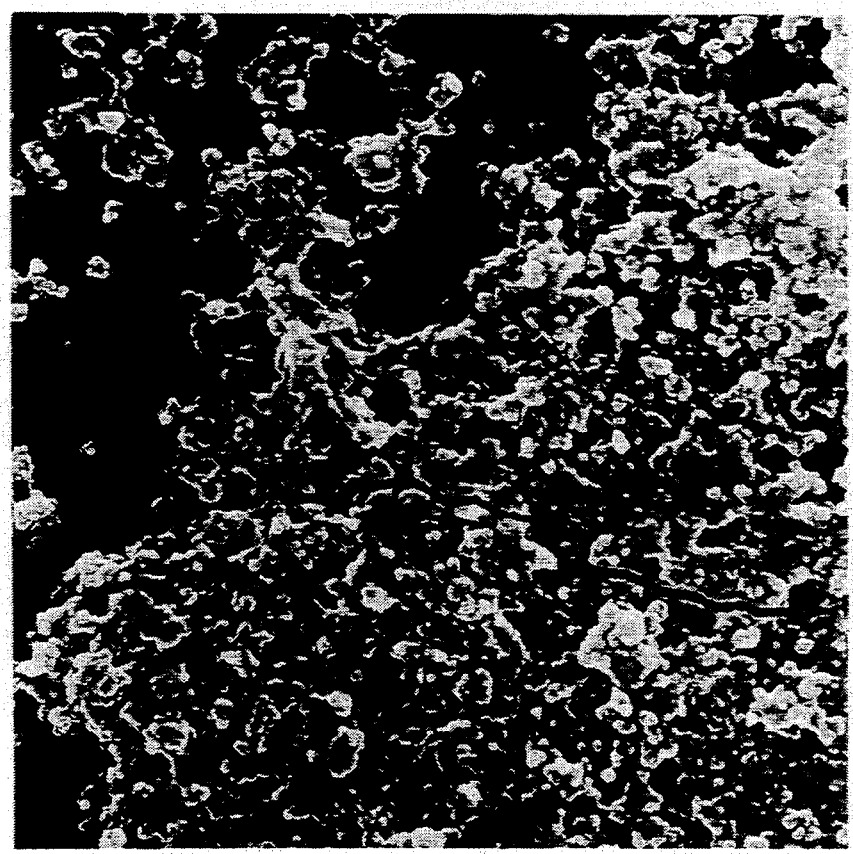
FIG. 6—Dextrinase-pretreated micrograph. A scanning electron micrograph picture showing a catheter surface pretreated or coated with dextrinase, upon exposure to staphylococci. The micrograph shows a thick biofilm layer with many coccal formations. These coccal formations are indicative of staphylococcal colonization.

No biofilm or organisms were observed on EDTA coated surfaces. However, biofilm formation was observed on catheter surfaces pretreated with dextrinase (FIGS. 4 and 5=saline; FIG. 3=EDTA; FIG. 6=Dextrinase pretreated).

EXAMPLE 8—MINOCYCLINE COATING OF A CATHETER AND MICROBIAL COLONIZATION

The present example is provided to demonstrate the anti-microbial colonization effect of minocycline at a catheter surface.

Catheter surfaces were coated with minocycline, vancomycin or control cement with $H_2O$, then the inventors exposed catheter surfaces to clinical staphylococci isolates using a Modified Robbin's Device. The Modified Robbin's Device simulates a vascular catheter, and therefore provides a model predictive of in vivo effects with regard to catheters coated according to the herein described studies in humans (see Example 2).

One gram of methylmethacrylate (cement) was mixed with 0.5 ml of sterile $H_2O$ and one of the following:
1. 60 mg of minocycline
2. 60 mg of vancomycin
3. control (cement+$H_2O$ alone)

Equal amounts of cement alone or with minocycline or vancomycin were put in the lumen of catheter latex segments in a specimen plug of the Modified Robbin's Device. Twenty-four hours later, a one-liter infusate bag made of 5% dextrose in water was infected with 5 ml of $10^5$ to $10^8$ colony forming units (CFU) per ml of slime producing *Staphylococcus epidermidis* strains obtained from the bloodstream of patients with catheter related bacteremia. Using a peristaltic pump, the infected infusate was run for 2 hours at a rate of 60 ml/hr through the catheter segments of the Modified Robbin's Device.

Each catheter segment was made of 30 $mm^2$ silicone with a lumen filled with cement. At the end of 2 hours, some catheter segments (control and antibiotics coated) were taken out from specimen plugs and the cement in the lumen was removed, then the surface that was exposed to the infected fluid was cultured semiquantitatively using the roll-plate technique. Other segments were left behind and flushed with saline solution for 4 hours, then cultured by roll-plate.

Electron microscopy was used to document the adherence of staphylococci and the formation of biofilm layer on the surface of control uncoated catheter segments. Leaching of antibiotics from the cement was demonstrated to occur for at least one week by determining the inhibition around disc-shaped pieces of cement placed on blood agar plates that had been inoculated with bacteria. Coating of the catheter segments with antibiotics was demonstrated by the zone of inhibition that continued to form for at least one week around the disc-shaped catheter segments (without cement) placed on agar plates that had been inoculated with bacteria. The results from this study are presented in Table 6.

TABLE 6

| Coating | No. colonies of *S. Epidermidis* from 30 $mm^2$ Catheter Surface | |
|---|---|---|
| | Before Flush | After Flush |
| Control | 336 | 128 |
| Vancomycin | 174 | 111 |
| Minocycline | 48 | 15 |

Figure 7:
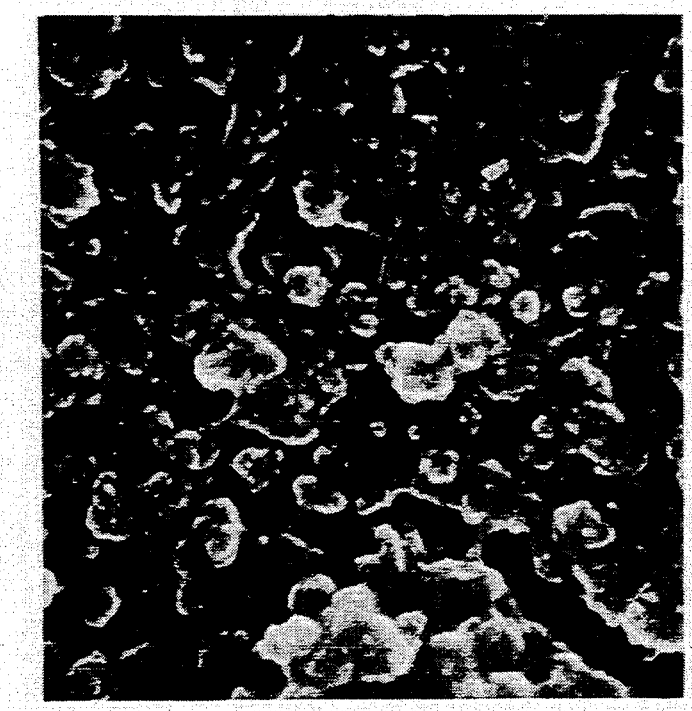
FIG. 7—Electron micrograph demonstrates formation of fibrous glycocalyx on the surface of a control (saline-treated) catheter segment—before flushing with saline for 4 hours.
Figure 8:
FIG. 8—Electron micrograph demonstrates some deranged fibrous glycocalyx on the surface of a minocycline coated catheter segment—before flushing with saline for 4 hours.
Figure 9:
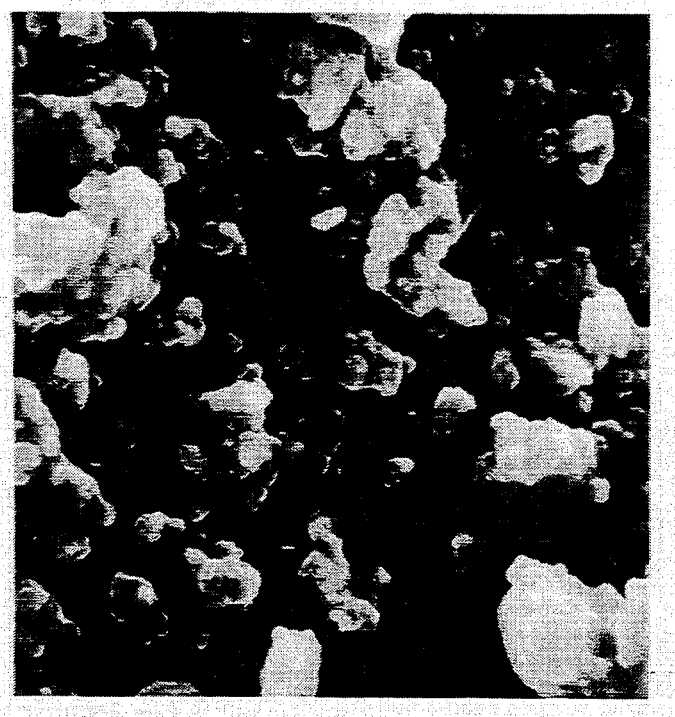
FIG. 9—Electron micrograph demonstrates fibrous glycocalyx on the surface of another control (saline-treated) catheter segment—after flushing with saline for 4 hours.
Figure 10:
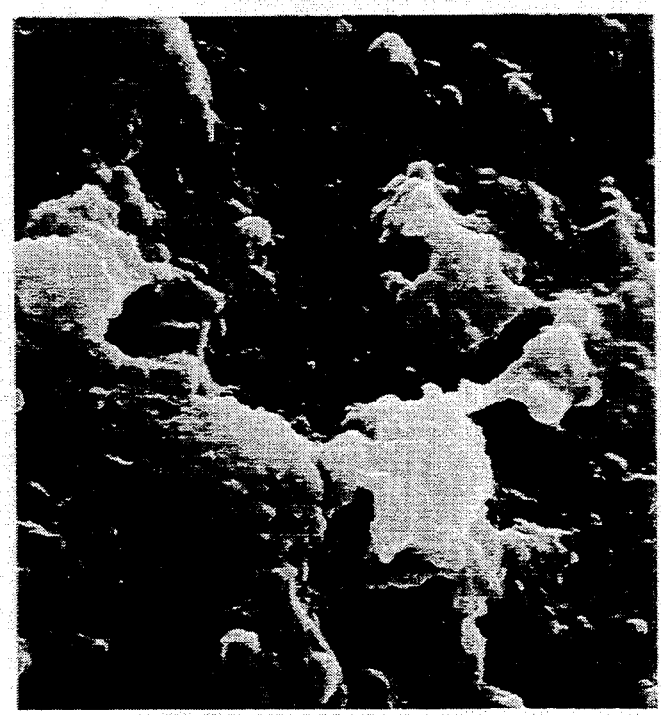
FIG. 10—Electron micrograph demonstrating fibrous glycocalyx on the surface of a minocycline-coated catheter segment—after flushing with saline for 4 hours.

Catheter segments coated with minocycline had a significantly lower number of adherent *Staphylococcus epidermidis* colonies, compared to control and vancomycin coated catheter segments (see Table 6). However, fibrous glycocalyx was not inhibited on the minocycline-coated catheter surfaces. The following scanning electron microscopic figures also evidenced these findings.
1. FIG. 7—shows fibrous glycocalyx on the surface of a control catheter segment—before flush.
2. FIG. 8—shows some deranged fibrous glycocalyx on the surface of minocycline coated catheter segment—before flush.
3. FIG. 9—shows fibrous glycocalyx on the surface of another control (saline) catheter segment after flush.
4. FIG. 10—shows fibrous glycocalyx on the surface of minocycline coated catheter segment after flush.

These data demonstrate that the coating of catheters with minocycline alone significantly reduced staphylococcal adherence. Fibrous glycocalyx formation is not inhibited with minocycline-coated surfaces.

EXAMPLE 9—STABILITY OF MINOCYCLINE AND EDTA PHARMACEUTICAL PREPARATIONS

The present study will be conducted to characterize the stability of the M-EDTA solutions of the present invention.

The M-EDTA solutions are expected to retain their potency for relatively long periods of time when stored refrigerated at about 4° C., i.e., for at least 1 month.

The solutions of the present invention have also been examined for retained potency at room temperature (37° C.). The M-EDTA solutions have been observed to retain relatively full potency for at least 72 hours at room temperature. It is therefore expected that the formulation has a shelf life that renders it suitable for routine hospital use (Table 1 and FIG. 11).

PROPHETIC EXAMPLE 10 PROPOSED COMPARATIVE CLINICAL TRIAL OF M-EDTA AND HEPARIN FOR THE PREVENTION OF CATHETER-RELATED INFECTIONS

The present prophetic example provides a proposed comparative study wherein the relative effectiveness of an M-EDTA solution compared to heparin (a currently used standard preparation) will be made for the prevention of catheter-related infections and occlusions.

Objective: To compare the safety and efficacy of M-EDTA flush solution with that of heparin in preventing infection and/or occlusion in central venous catheters (CVC).

Eligibility: Eligibility for enrollment into the study will be based on the following inclusion/exclusion criteria:

Inclusion Criteria
1. Patients must have a new ($\leq 7$ days old) functioning central venous catheter, utilized for infusion of chemotherapy, blood products, or other intermittent infusions.

2. Patients must be able to return to the outpatient clinic for evaluation in case of CVC occlusion or occurrence of fever.

3. Patients must have life expectancy for the planned duration of the study and must have catheter in place for study duration (study duration for a single patient is 6 months).

4. Catheters in the percutaneous/tunneled group will be limited to Hickman/Broviac.

Exclusion Criteria

1. Patients with an occluded central venous catheter.
2. Patients with any existing local or systemic catheter infection.
3. Patients with triple lumen catheters.
4. Patients with polyurethane or teflon catheters.
5. Patients currently taking warfarin.
6. Patients requiring previous catheter removal due to venous thrombosis.
7. It must be expected that the dwell time of 4 hours will not interfere with routine treatment of the underlying disease.
8. Patients with Groshong catheters.

Treatment Plan: Patients will be randomly assigned and in double blind manner to have their CVC flushed with either M-EDTA or Heparin according to the following:

1. Tunneled CVC (Hickman/Broviac) will receive either
   (a) two mls of M-EDTA (consisting of 3 mg of minocycline and 30 mg EDTA/ml) q daily
   (b) two mls of Heparin (100U/ml q daily)
2. Infusion ports will receive either
   (a) two mls of M-EDTA q 3 weeks
   (b) two mls of Heparin (100U/ml) q 3 weeks Endpoints and Treatment Evaluation: All patients will be followed up for 6 months and will be evaluated for 2 endpoints: catheter infection/colonization and occlusion. Catheter infection will include local CVC-related infection or systemic catheter-related septicemia. Catheter colonization will include positive quantitative catheter culture (flush technique) or positive quantitative blood culture through the CVC in the absence of a positive peripheral blood culture or clinical manifestations of sepsis (fever, chills or hypotension). Patients in the study who develop fever will be evaluated, and simultaneous quantitative blood cultures through CVC and peripheral vein conducted. Catheter occlusion will be categorized as complete or partial depending on whether one cannot withdraw blood, infuse fluids through the CVC, or both. This subgroup of infected catheters will be analyzed separately.

Statistical Considerations: Based on a recent surveillance study conducted by the inventors (see Table 7), the rate of CVC-related sepsis in pediatric oncology patients ranges from 15%–20.5% (see Table 6). Assuming a conservative total infection rate of 15% and assuming that M-EDTA will lower this rate to 5%, 140 patients will be required in each arm.

TABLE 7

| Infection Rates Associated with Hickman/Broviac Catheters and Implantable Ports in pediatric Oncology Patients, per 100 catheters | | | |
|---|---|---|---|
| Type of Infection | Hickman/ Broviac (N) | Port (N) | Total (N) |
| LOCAL CATHETER INFECTION | | | |

TABLE 7-continued

| Infection Rates Associated with Hickman/Broviac Catheters and Implantable Ports in pediatric Oncology Patients, per 100 catheters | | | |
|---|---|---|---|
| Type of Infection | Hickman/ Broviac (N) | Port (N) | Total (N) |
| Exit site or port infection | 17.9 (7) | 3.0 (3) | 7.2 (10) |
| Extraluminal infection (tip ≧ 15 cfu) | 0 (0) | 0 (0) | 0 (0) |
| Infection secondary to intraluminal colonization | 7.7 (3) | 3.0 (3) | 4.3 (6) |
| Tunnel tract infection | 2.6 (1) | N/A | 0.7 (1) |
| Total | 28.2 (11) | 6.0 (6) | 12.2 (17) |
| CATHETER-RELATED SEPSIS | | | |
| Definite | 7.7 (3) | 2.0 (2) | 3.6 (5) |
| Probable & physician diagnosed | 12.8 (5) | 13.0 (13) | 12.9 (18) |
| Total | 20.5 (8) | 15.0 (15) | 16.5 (23) |
| # Catheters | N = 39 | N = 100 | N = 139 |

The results from the proposed study will be employed in the development of a clinical protocol for the treatment and infection-free maintenance of indwelling catheters in humans.

PROPHETIC EXAMPLE 11—PREPARATION OF M-EDTA-COATED DEVICES FOR IN VIVO USE

The present example is provided to demonstrate the utility of the M-EDTA solution as a coating material for medical devices, most particularly catheters.

Any of a variety of coating techniques may be used for imparting a protective covering of the M-EDTA solution to a device. By way of example, such methods include.

Coating Methods for Medical Devices

As noted, preparations of the present invention may be advantageously used as a coating preparation for treating the surfaces of a medical device. The medical devices which are amendable to coatings with the subject M-EDTA preparations generally have surfaces composed of thermoplastic or polymeric materials such as polyethylene, Dacron, nylon, polyesters, polytetrafluoroethylene, polyurethane, latex, silicone elastomers and the like. Devices with metallic surfaces are also amenable to coatings with the disclosed combinations. Such devices, for example indwelling catheters of types listed herein, can be coated by cement mixture containing the subject antibiotic compounds. Particular devices especially suited for application of the M-EDTA preparation include intravascular, peritoneal, pleural and urological catheters; heart valves; cardiac pacemakers; vascular shunts; and orthopedic, intraocular, or penile prosthesis.

Various methods can be employed to coat the surfaces of medical devices with the M-EDTA preparation. For example, one of the simplest methods would be to flush the surfaces of the device with the M-EDTA preparation. Generally, coating the surfaces by a simple flushing technique would require convenient access to the implantable device. For example, catheters, are generally amenable to flushing with a solution of EDTA and minocycline. For use in flushing solutions, the effective concentration of minocycline would range from about 0.001 to 100 mg/ml, preferably about 3 mg/ml; and about 1 to 100 mg/ml EDTA, preferably about 30 mg/ml EDTA. The flushing solution would normally be further composed of a sterile water or a sterile normal saline solutions.

Another method of coating the devices would be to first apply or adsorb to the surface of the medical device a layer of tridodecylmethyl ammonium chloride (TDMAC) surfactant followed by a coating layer of the M-EDTA preparation. For example, a medical device having a polymeric surface, such as polyethylene, silastic elastomers, polytetrafluoroethylene or Darcon, can be soaked in a 5% by weight solution of TDMAC for 30 minutes at room temperature, air dried, and rinsed in water to remove excess TDMAC. Alternatively, TDMAC precoated catheters are commercially available; for example, arterial catheters coated with TDMAC are available from Cook Critical Care, Bloomington, Ind. The device carrying the adsorbed TDMAC surfactant coated can then be incubated in a solution of the M-EDTA combination for one hour or so, washed in sterile water to remove unbound M-EDTA and stored in a sterile package until ready for implantation. In general, the solution of M-EDTA includes between about 0.01 mg/ml–100 mg/ml EDTA (preferably 30 mg/ml) and between about 0.01 mg/ml–100 mg/ml minocyclines (preferably 3 mg/ml) in an aqueous pH 7.4–7.6 buffered solution or sterile water.

Alternative processes and reagents for bonding an agent contained in a solution to a surfactant-coated implantable medical device are provided in U.S. Pat. Nos. 4,442,133, 4,678,660 and 4,749,585, the entire contents of which are incorporated herein by reference for this purpose. A further method useful to coat the surface of medical devices with the subject antibiotic combinations involves first coating the selected surfaces with benzalkonium chloride followed by ionic bonding of the M-EDTA. See, e.g., Solomon, D. D. and Sherertz, R. J. (1987)[17] and U.S. Pat. No. 4,442,133[18].

Other methods of coating surfaces of medical devices with antibiotics are taught in U.S. Pat. No. 4,895,566 (a medical device substrate carrying a negatively charged group having a pKa of less than 6 and a cationic antibiotic bound to the negatively charged group); U.S. Pat. No. 4,917,686 (antibiotics are dissolved in a swelling agent which is adsorbed into the matrix of the surface material of the medical device); U.S. Pat. No. 4,107,121 (constructing the medical device with ionogenic hydrogels, which thereafter absorb or ionically bind antibiotics); U.S. Pat. No. 5,013,306 (laminating an antibiotic to a polymeric surface layer of a medical device); and U.S. Pat. No. 4,952,419 (applying a film of silicone oil to the surface of an implant and then contacting the silicone film bearing surface with antibiotic powders).

These and many other methods of coating the herein-described M-EDTA preparations to medical devices appear in numerous patents and medical journal articles. As is evident, one of ordinary skill having benefit of this disclosure would be apprised of several different methods of coating various medical device surfaces with the subject inventive minocycline and EDTA coatings.

Medical devices, particularly catheters of the type listed in Table 8, may be coated with the M-EDTA solution and then stored in a sterile packaging material until use.

TABLE 8

| SHORT-TERM TEMPORARY ACCESS CATHETER | LONG-TERM INDEFINITE VASCULAR ACCESS |
| --- | --- |
| Peripheral intravenous cannulas | Peripherally inserted central |

TABLE 8-continued

| SHORT-TERM TEMPORARY ACCESS CATHETER | LONG-TERM INDEFINITE VASCULAR ACCESS |
| --- | --- |
| winged steel needles peripheral intravenous catheters | venous catheters (PICC) |
| Arterial catheters | Percutaneous nontunneled silicone catheters |
| Central venous catheters | Cuffed tunneled central venous catheters (Hickman and Broviac) |
| Swan-Ganz catheters | Subcutaneous central venous ports (Infusaport, Port-a-cath, Landmark) |
| Hemodialysis catheters | |
| Umbilical catheters | |

PROPHETIC EXAMPLE 12 PROPOSED METHOD FOR MAINTAINING CATHETER PATENCY WITH MINOCYCLINE-EDTA PHARMACEUTICAL PREPARATION

The present example demonstrates one proposed embodiment of a method that may be used in maintaining the patency of an indwelling catheter in a patient. The regimen described herein is potentially applicable for use in both pediatric and adult patients, as the dose of M-EDTA in the regimen exposes patients only to relatively low, pharmaceutically acceptable levels of the EDTA and minocycline.

An indwelling catheter of a patient will be flushed with a solution of minocycline/EDTA. The "flushing" of the catheter will constitute filling the catheter with a volume of the M-EDTA solution sufficient to provide a concentration of about 9.0 mg minocycline and a concentration of about between 90 mg EDTA in the catheter. Assuming a catheter volume of about 2-3 ml., the solution will contain a concentration of EDTA of between about 10 mg/ml–30 mg/ml, and a concentration of minocycline of between about 1–3 mg/ml. "Flushing" the catheter with about 3 ml of the M-EDTA solution will thereby provide a dose of between 3–9 mg minocycline and about 30–90 mg EDTA. The solution of M-EDTA will be prepared as outlined in Example 1.

The "flushing" of the catheter is achieved by adding between 2–3 ml of the M-EDTA solution to the catheter. The solution is then allowed to diffuse through the catheter to the patient in which it is implanted. The concentration of the EDTA and minocycline in the solution is such that the patient will be exposed only to concentrations of the agents well below pharmacologically tolerable levels.

The flushing of the catheter is to be repeated at periodic intervals of at least every 72 hours (preferably, every 24 hours) to assure that infectious organisms are not allowed an opportunity to colonize the surface or initiate biofilm formation on the catheter surface.

BIBLIOGRAPHY

The following references are specifically incorporated herein by reference for the purposes indicated:

1. Harper, W. E. and Epis, J. A. (1987), Effect of chlorhexidine/EDTA/Tris against bacterial isolates from clinical specimens., *Microbios.*, 51:107–112.
2. Said, A. A. et al. (1987), Expression of H1 outer-membrane protein of *Pseudomonas aeruginosa* in relation to sensitivity to EDTA and polymyxin B., *J. Med. Microbiol.*, 24:267–274.
3. Root, J. L. et al. (1988), Inhibitory effect of disodium EDTA upon the growth of *Staphylococcus epidermi-*

*dis* in vitro: Relation to infection prophylaxis of Hickman catheters., *Antimicrob. Agents Chemother.*, 32:1627–1631.
4. Clumeck, N. et al. (1984), Treatment of severe staphylococcal infections with a rifampin-minocycline association., *J. Antimicrob. Chemother.*, 13(S):17–22.
5. Yourassowsky, E. et al. (1981), Combination of minocycline and rifampin against methicillin and gentamicin resistant *Staphylococcus aureus.*, *J. Clin. Pathol.*, 34:559–563.
6. Zinner, S. H. et al. (1981), Antistaphylococcal activity of rifampin with other antibiotics., *J. Infect. Dis.*, 144365–371.
7. Segreti, J. et al. (1989), In vitro activity of minocycline and rifampin against staphylococci., *Diagn. Microbiol. Infect. Dis.*, 12:253–255.
8. Yuk, J. H. et al. (1991), Minocycline as an alternative antistaphylococcal agent., *Rev. Infect. Dis.*, 13:1023–1024.
9. Root et al. (1988), Inhibitory Effect of Disodium EDTA upon the Growth of *Staphylococcus epidermidis* In Vitro: Relation to Infection Prophylaxis of Hickman Catheters., *Antimicrobial Agents and Chemotherapy*, 32(11):1627–1631.
10. Goodman and Gilman's *The Pharmacological Basis of Therapeutics*, 8th edition (1990), Pergamon Press
11. The Merck Index, 11th edition (1989), Merck & Co., Inc. Publishers, p. 1621.
12. Machnicka et al. (1986), *Folia Histochem. Cytobiol.*, 24(10): 65–70.
13. Tojo, M. et al. (1988), Isolation and characterization of a capsular polysaccharide adhesion from *Staphylococcus epidermidis.*, *J. Infect. Dis.*, 157:713–722.
14. Khoury, A. E. and Costerton, J. W. (1991), Bacterial biofilms in nature and disease. In: *Dialogues in Pediatric Urology*, 14:1–8.
15. Nickel, J. C. et al. (1985), Tobramycin Resistance of *Rseudomonas aeruginosa* Cells Growing as a Biofilm on Urinary Catheter Material., *Antimicrobial Agents and Chemotherapy*, 27:619–624.
16. Evans, R. C. and Holmes, C. J. (1987), Effect of Vancomycin Hydrochloride on *Staphylococcus epidermidis* Biofilm Associated with Silicone Elastomer., *Antimicrobial Agents and Chemotherapy*, 31:889–894.
17. Solomon et al. (1987), *J. Controlled Release*, 6:343–352.
18. U.S. Pat. No. 4,442,133.
19. U.S. Pat. No. 4,678,660.
20. U.S. Pat. No. 4,749,585.
21. U.S. Pat. No. 4,895,566.
22. U.S. Pat. No. 4,917,686.
23. U.S. Pat. No. 4,107,121.
24. U.S. Pat. No. 5,013,306.
25. U.S. Pat. No. 4,952,419.

What is claimed is:

1. A catheter flushing pharmaceutical preparation comprising a pharmacologically effective amount of minocycline and an antimicrobially effective amount of EDTA in a carrier solution.

2. The pharmaceutical preparation of claim 1 wherein the catheter is an indwelling catheter.

3. The pharmaceutical preparation of claim 2 wherein the indwelling catheter is a central venous catheter, a peripheral intravenous catheter, an arterial catheter, a Swan-Ganz catheter, a hemodialysis catheter, an umbilical catheter, a percutaneous nontunneled silicone catheter, a cuffed tunneled central venous catheter or a subcutaneous central venous port.

4. The pharmaceutical preparation of claim 1 wherein the indwelling catheter is urinary catheter or a peritoneal catheter.

5. The pharmaceutical preparation of claim 1 wherein the pharmacologically effective amount of minocycline is about 3 mg/ml and the pharmacologically effective amount of EDTA is about 30 mg/ml in the carrier solution.

6. The pharmaceutical preparation of claim 1 wherein the carrier solution is saline.

7. An anti-microbial flushing pharmaceutical preparation comprising a glycocalyx inhibiting concentration of EDTA and minocycline in a pharmaceutically acceptable carrier solution.

8. The catheter flushing pharmaceutical preparation of claim 7 wherein the preparation comprises EDTA and minocycline in a pharmaceutically acceptable carrier solution.

9. The catheter flushing pharmaceutical preparation of claim 8 wherein the concentration of EDTA is between about 10–100 mg/ml and the concentration of minocycline is between about 0.001–100 mg/ml.

10. The catheter flushing pharmaceutical preparation of claim 8 wherein the concentration of EDTA is about 30 mg/ml and the concentration of minocycline is about 3 mg/ml.

11. The catheter flushing pharmaceutical preparation of claim 7 or 8 wherein the carrier solution is saline.

12. The catheter flushing pharmaceutical preparation of claim 7 or 8 wherein the formulation inhibits the formation of polysaccharide-rich glycocalyx.

13. The catheter flushing pharmaceutical preparation of claim 1 wherein the amount of EDTA is between about 10–100 mg/ml and the amount of minocycline is between about 0.001–100 mg/ml of the preparation.

14. The anti-microbial flushing pharmaceutical of claim 7 wherein the amount of EDTA is between about 10–100 mg/ml and the amount of minocycline is between about 0.001–100 mg/ml of the preparation.

* * * * *

UNITED STATES PATENT AND TRADEMARK OFFICE
CERTIFICATE OF CORRECTION

PATENT NO. : 5,362,754
DATED : November 8, 1994
INVENTOR(S) : Issam Raad et al.

It is certified that error appears in the above-indentified patent and that said Letters Patent is hereby corrected as shown below:

At column 1, line 39, delete "such".

At column 1, line 41, before the word 'slimy' insert -- a --.

At column 2, line 9-10, delete "M-EDTA" and substitute therefor -- M EDTA --.

At column 3, line 18, before the word "bacteremias", insert -- of --.

At column 5, line 52, before the word "is", delete "inducted" and substitute therefor --included--.

At column 6, line 42, before the word "exposed", insert -- was --.

Col. 20, line 5, delete "an antimicrobally" and substitute therefor -- a pharmacologically --

Col. 20, line 22, delete "in the carrier solution."

Col. 20, line 35, delete "8" and substitute therefor -- 7 --.

Col. 20, line 39, delete "8" and substitute therefor -- 7 --.

Col. 20, line 43, delete "or 8".

Col. 20, line 45, delete "or 8".

UNITED STATES PATENT AND TRADEMARK OFFICE
CERTIFICATE OF CORRECTION

PATENT NO. : 5,362,754
DATED : November 8, 1994
INVENTOR(S) : Issam Raad et al.

It is certified that error appears in the above-indentified patent and that said Letters Patent is hereby corrected as shown below:

Column 20, line 51, after the word "pharmaceutical", insert --preparation--, line 53, delete "about 10-100", and substitute therefore --20-60--, and line 54, delete "about 0.001-100" and substitute therefore --2-9--.

Signed and Sealed this

Twenty-third Day of May, 1995

BRUCE LEHMAN

Attest:

Attesting Officer

Commissioner of Patents and Trademarks

US005362754B1

REEXAMINATION CERTIFICATE (3961st)

United States Patent [19]
Raad et al.

[11] B1 5,362,754
[45] Certificate Issued Dec. 21, 1999

[54] M-EDTA PHARMACEUTICAL PREPARATIONS AND USES THEREOF

[75] Inventors: Issam Raad, Houston, Tex.; Robert J. Sherertz, Winston-Salem, N.C.

[73] Assignee: The University of Texas System Board of Regents, Austin, Tex.

Reexamination Request:
No. 90/005,155, Oct. 23, 1998

Reexamination Certificate for:
Patent No.: 5,362,754
Issued: Nov. 8, 1994
Appl. No.: 07/975,486
Filed: Nov. 12, 1992

[51] Int. Cl.$^6$ .......................... A01N 37/12; A01N 25/08; A61M 31/00
[52] U.S. Cl. .......................... 514/566; 514/836; 424/405; 604/53
[58] Field of Search ...................................... 514/566, 836; 424/405; 604/53

[56] References Cited

PUBLICATIONS

A.D. Russell, Inhibition and Destruction of the Microbial Cell, *EDTA–Drug Combinations*, p. 209–244 (1971).

Wooley et al., "In Vitro Action of Combinations of Antimicrobial Agents and EDTA–Tromethamine on *Escherichia coli*", *Am J. Vet Res*, 44(6):1154–58 (1982).

Wooley et al., "In Vitro Action of Combinations of Antimicrobial Agents and EDTA–Tromethamine on *Pseudomonas Aeruginosa*", *Am J. Vet Res*, 44(8):1521–24 (1982).

Tyler et al., *Pharmacognosy*, Eighth Edition, p. 367–371 (1981).

Susan Budavari, Editor, *The Merck Index; An Encyclopedia of Chemical, Drugs and Biologicals*, Twelfth Edition, p. 1061 (1996).

Wiernikowski et al., "Bacterial Colonization of Tunneled Right Atrial Catheters in Pediatric Oncology: A Comparison of Sterile Saline and Bacteriostatic Saline Flush Solutions", *Am J. Pediatr Hematol Oncol.* 13(2):137–140 (1991).

Schwartz et al., "Prevention of Bacteremia Attributed to Luminal Colonization of Tunneled Central Venous Catheters With Vancomycin–Susceptible Organisms", *Journal of Clinical Oncology*, 8(9):1591–1597 (1990).

Kamal et al., "Reduced Intravascular Catheter Infection by Antibiotic Bonding", *JAMA*, May 8, 1991, 265(18):2364–68 (1991).

Mandell et al, *Principles and Practice of Infectious Diseases*, Third Edition, p. 2189–96 (1990).

*Primary Examiner*—Carlos Azpuru

[57] ABSTRACT

Disclosed are pharmaceutical compositions of a mixture of minocycline and EDTA (M-EDTA) and methods of using the compositions in maintaining the patency of a catheter port. Methods for inhibiting the formation of polysaccharide-rich glycocalyx (such as the glycocalyx of staphylococcal organisms) are also provided using an M-EDTA solution. The M-EDTA solution may also be used to pretreat a medical device to prevent adherence of infectious organisms, such as *S. epidermidis* and *S. aureus*. The compositions destroy and prevent the formation of polysaccharide-rich glycocalyx. Methods for treating infections of *S. epidermidis* and *S. aureus* where glycocalyx formation are provided with an M-EDTA solution. The minocycline and EDTA solutions are included together within a pharmacologically acceptable carrier solution, such as saline.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–14 is confirmed.

* * * * *